United States Patent [19]

Murata et al.

[11] 4,186,148

[45] Jan. 29, 1980

[54] PROCESS FOR PRODUCING 3,7-DIMETHYL-2,6-OCTADIENYLAMINE DERIVATIVES

[75] Inventors: Atsuo Murata; Shuji Tsuchiya; Akihiro Konno; Jun Uchida, all of Funabashi, Japan

[73] Assignee: Nissan Chemical Industries Limited, Tokyo, Japan

[21] Appl. No.: 902,758

[22] Filed: May 3, 1978

[30] Foreign Application Priority Data

May 11, 1977 [JP] Japan .................................. 52-54045

[51] Int. Cl.$^2$ ...................... C07C 85/18; C07D 295/02
[52] U.S. Cl. ............................ 260/583 H; 252/429 R; 260/326.8; 544/178; 546/349
[58] Field of Search .......... 260/583 H, 585 R, 585 D, 260/326.8; 252/429 R; 544/178; 546/349

[56] References Cited

U.S. PATENT DOCUMENTS

| | | | |
|---|---|---|---|
| 2,501,509 | 3/1950 | Gresham et al. ................. | 260/583 H |
| 2,726,980 | 12/1955 | Goodhue et al. ........... | 260/585 D X |
| 3,502,725 | 3/1970 | Dewhirst et al. ............ | 260/583 H X |
| 3,530,187 | 9/1970 | Shryne .............................. | 260/583 H |
| 3,872,153 | 3/1975 | Wright et al. ................ | 260/583 H X |
| 4,100,194 | 7/1978 | Hobbs et al. ................. | 260/583 H X |
| 4,100,196 | 7/1978 | Hobbs et al. ..................... | 260/585 D |

FOREIGN PATENT DOCUMENTS

| | | | |
|---|---|---|---|
| 1078114 | 3/1960 | Fed. Rep. of Germany ...... | 260/583 H |
| 1093353 | 11/1960 | Fed. Rep. of Germany ...... | 260/583 H |
| 51-4109 | 1/1976 | Japan .................................. | 260/583 H |
| 51-70707 | 6/1976 | Japan .................................. | 260/583 H |

OTHER PUBLICATIONS

Noren, "J. Org. Chem.", vol. 40, No. 7, pp. 967–968, (1975).
Martirosyan et al., "J. Org. Chem. (USSR)", vol. 6, pp. 446–449 (1970).
Baker et al., "J. Chem. Soc., Perkin Trans. II", pp. 1511–1517 (1974).

*Primary Examiner*—John Doll
*Attorney, Agent, or Firm*—Oblon, Fisher, Spivak, McClelland & Maier

[57] ABSTRACT

3,7-Dimethyl-2,6-octadienylamine derivatives are produced by reacting isoprene with a secondary amine in the presence of a catalyst prepared by reacting a secondary amine, a conjugated diene and/or a polycyclic aromatic compound, a lithium salt and sodium and/or potassium metal.

13 Claims, No Drawings

PROCESS FOR PRODUCING 3,7-DIMETHYL-2,6-OCTADIENYLAMINE DERIVATIVES

BACKGROUND OF THE INVENTION

The present invention relates to a process for selectively producing 3,7-dimethyl-2,6-octadienylamine derivative by reacting isoprene with a secondary amine in the presence of a novel catalyst.

The inventors have studied to selectively produce terpenes from isoprene in high yield. As the results, the inventors have found to selectively produce 3,7-dimethyl-2,6-octadienylamine derivatives in high yield by using the novel catalyst and the starting materials. The present invention has been attained by the finding.

SUMMARY OF THE INVENTION

It is an object of the present invention to provide a process for selectively producing 3,7-dimethyl-2,6-octadienylamine derivative in high yield with the novel catalyst which is significantly economical.

The foregoing and other objects of the present invention have been attained by reacting isoprene with a secondary amine in the presence of a catalyst produced by reacting a secondary amine, a conjugated diene and/or a polycyclic aromatic compound, a lithium salt and sodium and/or potassium metal.

DETAILED DESCRIPTION OF THE PREFERRED EMBODIMENTS

The catalyst used in the present invention will be further illustrated.

A soluble lithium catalyst is not formed by a lithium salt itself. However, the soluble lithium catalyst can be formed by a combination of the lithium salt with sodium or potassium metal to impart the catalytic activity.

It has been known to produce 3,7-dimethyl-2,6-octadienylamine derivatives by using n-butyl lithium catalyst (Japanese Unexamined Patent Publication No. 48610/1974) or using a catalyst produced by reacting lithium metal, a conjugated diene and a secondary amine (Japanese Unexamined Patent Publication No. 4109/1976).

Thus, n-butyl lithium and lithium metal are quite expensive and sensitive to air and a moisture, loss of the catalyst is easily caused and the handling of the catalyst is not easy, disadvantageously.

In accordance with the present invention, the catalyst can be produced by using a lithium salt which is economical and easily treated, and sodium and/or potassium metal which is economical, instead of lithium metal.

3,7-Dimethyl-2,6-octadienylamine derivatives can be easily obtained by using such catalyst.

The secondary amines used in the present invention are chained or cyclic amines having carbon atoms or hetero-atoms.

Suitable secondary amines include chained amines such as dimethylamine, diethylamine, di-n-propylamine and di-n-butylamine; and cyclic amines such as piperidine, pyrrolidine and morpholine.

The secondary amine used in the preparation of the catalyst is preferably the secondary amine used as the raw material for the production of 3,7-dimethyl-2,6-octadienylamine derivative from the viewpoint of the reaction operation and the purification of the reaction product.

The amount of the secondary amine used in the preparation of the catalyst should be more than equimolar to that of sodium and/or potassium metal. It is preparable to use the secondary amine used for the production of 3,7-dimethyl-2,6-octadienylamine derivatives.

It is preferable to use 5 to 50 moles of the secondary amine per 1 mole of sodium and/or potassium metal.

The unsaturated hydrocarbons of the conjugated dienes and/or polycyclic aromatic compounds used in the present invention are as follows.

Suitable conjugated diene compounds include conjugated dienes such as butadiene, isoprene and 1,3-pentadiene and conjugated olefin with aromatic compound such as styrene and α-methylstyrene.

Suitable polycyclic aromatic compounds include naphthalene, anthracene and diphenyl.

One or two compounds can be used. An amount of the compound is preferably in the range of $\frac{1}{2}$ to 8 moles to 1 mole of sodium and/or potassium metal.

The special characteristic compound used in the present invention is a lithium salt such as lithium halide.

The amount of the lithium salt is preferably in the range of 1 to 10 moles per 1 mole of sodium and/or potassium metal.

When the amount of the lithium salt is less than the equimolar to that of sodium or potassium metal, excess of sodium metal or organosodium compound remains in the catalyst. Such excessive sodium metal or organosodium compound remained in the catalyst causes the side-reaction for producing by-products and higher polymers in the production of 3,7-dimethyl-2,6-octadienylamine derivatives, to impart the adverse effect in the reaction.

The amount of sodium and/or potassium metal is not limited. Thus, it is preferable to use 0.02 0.2 mole of sodium and/or potassium metal per 1 mole of the secondary amine as the raw material for the production of 3,7-dimethyl-2,6-octadienylamine derivatives.

It is not always necessary to use a solvent in the preparation of the catalyst. Thus, it is preferable to use a solvent.

Suitable solvents include saturated hydrocarbons such as n-hexane, n-octane and cyclohexane; aromatic compounds such as benzene, and tertiary amines such as triethylamine.

The solvent can be also used in the production of 3,7-dimethyl-2,6-octadienylamine derivatives.

The temperature in the preparation of the catalyst is usually in the range of −20 to 100° C. preferably 0° to 60° C. The degree of the formation of the catalyst can be found by the degree of the dissolution of sodium and/or potassium metal. It is necessary to prepare the catalyst in an inert atmosphere.

It is important to perform the reaction of isoprene with the secondary amine to produce 3,7-dimethyl-2,6-octadienylamine derivative after the preparation of the catalyst.

Isoprene is added to the catalyst or the catalyst is added to isoprene. An amount of isoprene is usually more than 2 moles preferably 3 to 8 moles per 1 mole of the secondary amine as the raw material for the production of 3,7-dimethyl-2,6-octadienylamine derivatives.

The reaction temperature in the production of 3,7-dimethyl-2,6-octadienylamine derivatives is usually in a range of 10° to 130° C. preferably 40° to 100° C.

It is preferable perform the reaction for producing 3,7-dimethyl-2,6-octadienylamine derivative in an inert atmosphere.

After the reaction, the catalyst is inactivated by adding an alcohol, water or $CO_2$ and 3,7-dimethyl-2,6-octadienylamine derivative can be obtained by the conventional distillation.

The present invention will be further illustrated by certain examples.

EXAMPLE 1

In a 100 ml. pressure glass reactor, 1.36 g (0.02 mole) of isoprene, 7.3 g (0.1 mole) of diethylamine, 2 g of cyclohexane, 0.21 g (0.005 mole) of LiCl and 0.07 g (0.003 mole) of sodium metal were charged and the catalyst solution was prepared by reacting them at 30° C. for 1 hour in nitrogen atmosphere. Sodium metal was completely dissolved.

To the catalyst solution added 8 g of cyclohexane and 34 g (0.5 mole) of isoprene and the reaction of them was performed at 65° C. for 1 hour and at 80° C. for 3 hours in nitrogen atmosphere. Ethanol was added to the reaction mixture to inactivate the catalyst and the amount of 3,7-dimethyl-2,6-octadienyl diethylamine was measured by the gas chromatography. The yield of 3,7-dimethyl-2,6-octadienyl diethylamine based on the secondary amine was 75%.

EXAMPLE 2

In a 100 ml. pressure glass reactor, 1.36 g (0.02 mole) of isoprene, 7.3 g (0.1 mole) of diethylamine and 1.00 g (0.0076 mole) of LiI and 0.15 g (0.0065 mole) of sodium metal were charged and the catalyst solution was prepared by reacting them at 30° C. for 1 hour in nitrogen atmosphere.

To the catalyst solution added 10 g of cyclohexane and 34 g of isoprene and the reaction was performed at 65° C. for 1 hour and at 80° C. for 4 hours in nitrogen atmosphere and the reaction mixture was treated in accordance with the process of Example 1. The yield of 3,7-dimethyl-2,6-octadienyl diethylamine was 85%.

EXAMPLE 3

In a 100 ml. pressure glass reactor, 1.36 g (0.02 mole) of isoprene, 7.3 g (0.1 mole) of diethylamine, 0.65 g (0.0075 mole) of LiBr and 0.12 g (0.0052 mole) of sodium metal were charged and the catalyst solution was prepared by reacting them at 30° C. for 45 minutes. To the catalyst solution added 10 g of cyclohexane and 34 g of isoprene and the reaction was performed at 80° C. for 3 hours in nitrogen atmosphere, and the reaction mixture was treated in accordance with the process of Example 1. The yield of 3,7-dimethyl-2,6-octadienyl diethylamine was 69%.

EXAMPLE 4

In a 100 ml. pressure glass reactor, 2.43 g (0.036 mole) of isoprene, 4.02 g (0.089 mole) of dimethylamine, 2 g of cyclohexane, 0.38 g (0.009 mole) of LiCl and 0.11 g (0.0048 mole) of sodium metal were charged and the catalyst solution was prepared by reacting them at 40° C. for 10 minutes.

To the catalyst solution added 8 g of cyclohexane and 30.4 g (0.447 mole) of isoprene and the reaction was performed at 65° C. for 5 hours in nitrogen atmosphere and the reaction mixture was treated in accordance wih the process of Example 1. The yield of 3,7-dimethyl-2,6-octadienyl diethylamine was 59%.

EXAMPLE 5

In a 100 ml. pressure glass reactor, 2.56 g (0.02 mole) of naphthalene, 7.3 g (0.1 mole) of diethylamine, 0.63 g (0.015 mole) of LiCl and 0.18 g (0.008 mole) of sodium metal were charged and the catalyst solution was prepared by reacting them at 15° C. for 2 hours.

To the catalyst solution added 10 g of cyclohexane and 34 g (0.5 mole) of isoprene and the reaction was performed at 80° C. for 5 hours in nitrogen atmosphere and the reaction mixture was treated in accordance with the process of Example 1. The yield of 3,7-dimethyl-2,6-octadienyl diethylamine was 77%.

What is claimed is:

1. A process for producing a 3,7-dimethyl-2,6-octadienylamine compound comprising: reacting isoprene with a secondary amine in the presence of a catalyst prepared by reacting a secondary amine, a conjugated diene and/or a polycyclic aromatic compound, a lithium salt and sodium and/or potassium metal.

2. The process according to claim 1 wherein isoprene is reacted with said secondary amine in a ratio of more than 2 moles of isprene per 1 mole of the secondary amine.

3. The process according to claim 1 wherein the reaction of isoprene with the secondary amine is performed at 10° to 130° C.

4. The process according to claim 1, wherein in the preparation of the catalyst the conjugated diene and/or the polycyclic aromatic compound is present in a molar ratio of ½ to 8 relative to the sodium and/or potassium metal.

5. The process according to claim 1, wherein in the preparation of the catalyst the lithium salt is present in a molar ratio of 1 to 10 relative to the sodium and/or potassium metal.

6. The process according to claim 1, wherein in the preparation of the catalyst the sodium and/or potassium metal is present in a molar ratio of 0.02 to 0.2 relative to the secondary amine used in the production of the 3,7-dimethyl-2,6-octadienylamine derivative.

7. The process according to claim 1 wherein the secondary amine used in the preparation of the catalyst is the same as the secondary amine used in the production of 3,7-dimethyl-2,6-octadienylamine derivative.

8. The process of claim 1, wherein said reaction between isoprene and said secondary amine is conducted in the presence of an inert solvent.

9. The process of claim 1, wherein said conjugated diene is isoprene, butadiene, 1,3-pentadiene, styrene or α-methylstyrene.

10. The process of claim 1, wherein said polycyclic aromatic compound is naphthalene, diphenyl or anthracene.

11. The process of claim 1, wherein said catalyst is prepared at a temperature ranging from −20° to 100° C.

12. A process for producing a 3,7-dimethyl-2,6-octadienylamine compound, comprising: reacting isoprene with a secondary amine in the presence of a catalyst prepared by reacting a secondary amine, a conjugated diene and/or a polycyclic aromatic compound, a lithium halide and sodium and/or potassium metal.

13. A process for producing a 3,7-dimentyl-2,6-octadienylamine compound, comprising: reacting isoprene with a secondary amine in the presence of a catalyst prepared by reacting a secondary amine, a lithium salt, sodium and/or potassium metal and a material selected from the group consisting of a polycyclic aromatic compound and a mixture of a polycyclic aromatic compound and a conjugated diene.

* * * * *